(12) United States Patent
Auerbach et al.

(10) Patent No.: US 8,728,749 B2
(45) Date of Patent: May 20, 2014

(54) DETECTION OF LCAT ACTIVITY

(76) Inventors: Bruce J. Auerbach, Ann Arbor, MI (US); Reynold Homan, Ann Arbor, MI (US); Brian Krause, Ann Arbor, MI (US)

( * ) Notice: Subject to any disclaimer, the term of this patent is extended or adjusted under 35 U.S.C. 154(b) by 0 days.

(21) Appl. No.: 13/977,161

(22) PCT Filed: Dec. 28, 2011

(86) PCT No.: PCT/US2011/067571
§ 371 (c)(1),
(2), (4) Date: Oct. 9, 2013

(87) PCT Pub. No.: WO2012/092365
PCT Pub. Date: Jul. 5, 2012

(65) Prior Publication Data
US 2014/0024061 A1  Jan. 23, 2014

Related U.S. Application Data

(60) Provisional application No. 61/428,925, filed on Dec. 31, 2010.

(51) Int. Cl.
*C12Q 1/48* (2006.01)

(52) U.S. Cl.
USPC .................................................. 435/15

(58) Field of Classification Search
USPC .................................................. 435/15
See application file for complete search history.

(56) References Cited

PUBLICATIONS

Bonelli et al., J. Lipid Res., 33, 1863-1869, 1992.*

* cited by examiner

*Primary Examiner* — Maryam Monshipouri

(57) ABSTRACT

The present disclosure relates to methods for detecting and measuring the activity of lecithin:cholesterol acyltransferase (LCAT) in solution (e.g. serum, plasma, cell culture media, aqueous solution) with fluorescent sterol substrates. The present disclosure also relates to a method for evaluating efficacy of a therapeutic agent for stimulating LCAT and for determining endogenous LCAT activity in a patient. Also disclosed are kits that are used to carry out the aforementioned methods and methods.

7 Claims, 5 Drawing Sheets

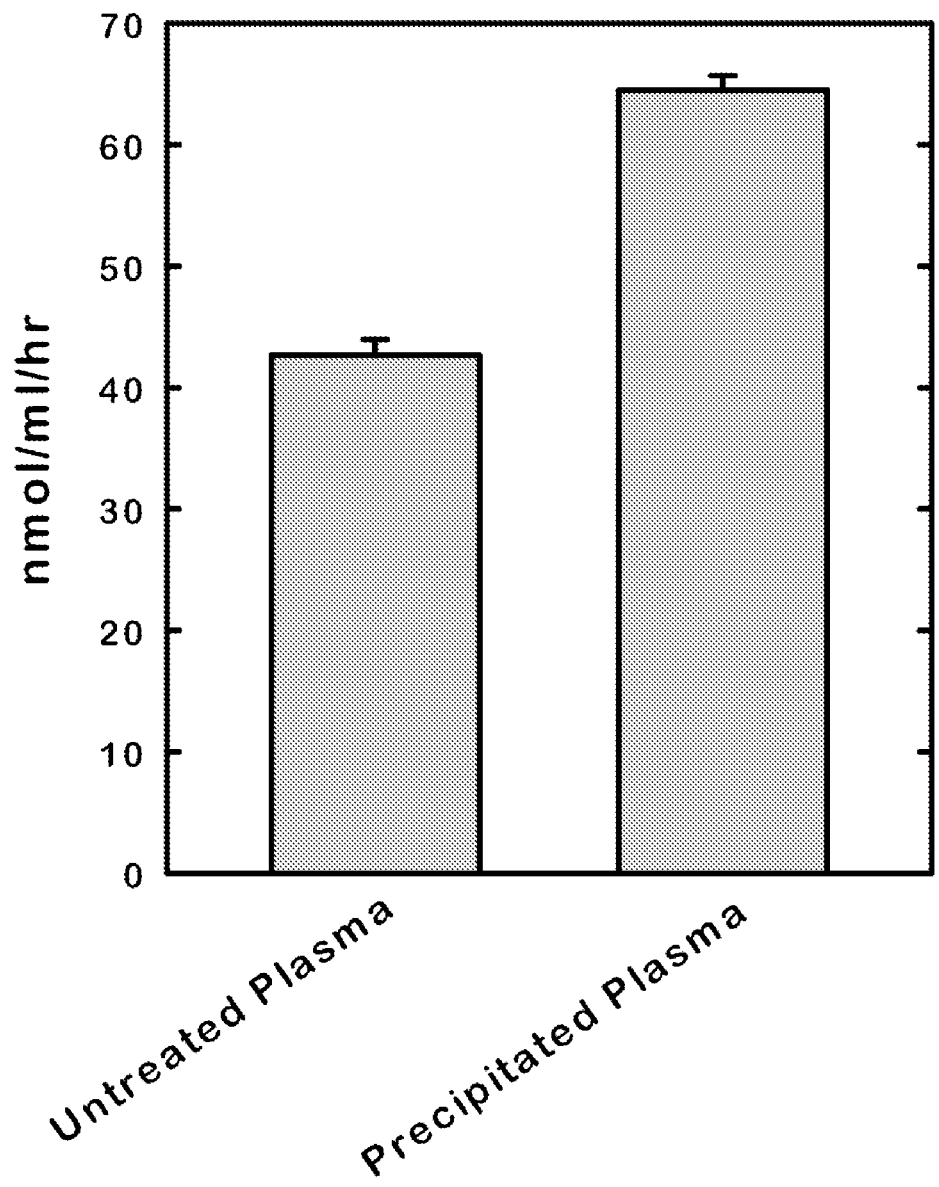

SEQUENCE LISTING

```
<160> NUMBER OF SEQ ID NOS: 63

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 1

Pro Val Leu Asp Leu Phe Arg Glu Leu Leu Asn Glu Leu Leu Glu Ala
1               5                   10                  15

Leu Lys Gln Lys Leu Lys
            20
```

```
<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 2

Pro Thr Leu Asp Leu Phe Arg Glu Leu Leu Asn Glu Leu Leu Glu Ala
1               5                   10                  15

Leu Lys Gln Lys Leu Lys
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 3

Pro Ser Leu Asp Leu Phe Arg Glu Leu Leu Asn Glu Leu Leu Glu Ala
1               5                   10                  15

Leu Lys Gln Lys Leu Lys
            20

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 4

Pro Val Leu Asp Leu Phe Arg Glu Leu Leu Asn Glu Leu Leu Gln Lys
1               5                   10                  15

Leu Lys Lys

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 5

Pro Thr Leu Asp Leu Phe Arg Glu Leu Leu Asn Glu Leu Leu Gln Lys
1               5                   10                  15

Leu Lys Lys

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 6

Pro Val Leu Asp Leu Phe Arg Glu Leu Leu Glu Glu Leu Leu Gln Lys
1               5                   10                  15
```

Leu Lys Lys

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 7

Pro Val Leu Asp Leu Phe Lys Glu Leu Leu Glu Glu Leu Phe Gln Lys
1               5                   10                  15

Leu Lys Lys

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 8

Pro Val Leu Asp Lys Phe Leu Glu Leu Leu Glu Glu Leu Phe Gln Lys
1               5                   10                  15

Leu Lys Lys

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 9

Glu Trp Leu Lys Ala Phe Leu Glu Lys Val Leu Glu Lys Leu Lys Glu
1               5                   10                  15

Leu Phe

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 10

Glu Trp Leu Lys Ala Phe Tyr Glu Lys Val Leu Glu Lys Leu Lys Glu
1               5                   10                  15

```
<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 11

Asp Trp Leu Lys Ala Phe Tyr Asp Lys Val Phe Glu Lys Phe Lys Glu
1               5                   10                  15

Phe Phe

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 12

Glu Val Leu Lys Asn Leu Leu Glu Lys Leu Leu Glu Lys Leu Lys Glu
1               5                   10                  15

Leu Phe

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 13

Asp Leu Trp Gln Arg Leu Leu Glu Leu Phe Asn Glu Leu Leu Glu Lys
1               5                   10                  15

Leu Lys Gln Ala Leu Lys
                20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 14

Asp Val Phe Gln Ala Leu Lys Glu Leu Phe Ala Gln Leu Leu Glu Lys
1               5                   10                  15

Trp Lys Gln Val
                20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
                                      amphipathic peptide

<400> SEQUENCE: 15

Pro Val Leu Asp Leu Phe Arg Glu Leu Leu Asn Glu Leu Leu Glu Leu
1               5                   10                  15

Lys Gln Lys Leu Lys
            20

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 16

Gly Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 17

Pro Val Leu Asp Leu Phe Arg Glu Leu Leu Asn Glu Leu Leu Glu Trp
1               5                   10                  15

Leu Lys Gln Lys Leu Lys
            20

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 18

Pro Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 19

Pro Val Leu Asp Leu Phe Arg Glu Leu Leu Asn Glu Leu Glu Ala Leu
1               5                   10                  15

Lys Gln Lys Leu Lys
            20

<210> SEQ ID NO 20
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 20

Pro Val Leu Asp Leu Phe Lys Glu Leu Leu Asn Glu Leu Leu Glu Ala
1               5                   10                  15

Leu Lys Gln Lys Leu Lys
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 21

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 22

Pro Val Leu Asp Leu Phe Arg Glu Leu Gly Asn Glu Leu Leu Glu Ala
1               5                   10                  15

Leu Lys Gln Lys Leu Lys
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 23

Pro Val Leu Asp Leu Phe Arg Glu Leu Leu Asn Glu Leu Leu Glu Ala
1               5                   10                  15

Lys Gln Lys Leu Lys
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 24

Pro Val Leu Asp Leu Phe Lys Glu Leu Leu Gln Glu Leu Leu Glu Ala
1               5                   10                  15
```

```
Leu Lys Gln Lys Leu Lys
            20

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 25

Pro Val Leu Asp Leu Phe Arg Glu Leu Leu Asn Glu Leu Leu Glu Ala
1               5                   10                  15

Gly Lys Gln Lys Leu Lys
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 26

Gly Val Leu Asp Leu Phe Arg Glu Leu Leu Asn Glu Gly Leu Glu Ala
1               5                   10                  15

Leu Lys Gln Lys Leu Lys
            20

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<221> NAME/KEY: MOD_RES
<222> LOCATION: (18)..(18)
<223> OTHER INFORMATION: Ornithine
<220> FEATURE:
<221> NAME/KEY: MOD_RES
<222> LOCATION: (20)..(20)
<223> OTHER INFORMATION: Ornithine
<220> FEATURE:
<221> NAME/KEY: MOD_RES
<222> LOCATION: (22)..(22)
<223> OTHER INFORMATION: Ornithine

<400> SEQUENCE: 27

Pro Val Leu Asp Leu Phe Arg Glu Leu Leu Asn Glu Leu Leu Glu Ala
1               5                   10                  15

Leu Xaa Gln Xaa Leu Xaa
            20

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 28

Pro Val Leu Asp Leu Phe Arg Glu Leu Trp Asn Glu Leu Leu Glu Ala
1               5                   10                  15
```

```
Leu Lys Gln Lys Leu Lys
            20

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 29

Pro Val Leu Asp Leu Leu Arg Glu Leu Leu Asn Glu Leu Leu Glu Ala
1               5                   10                  15

Leu Lys Gln Lys Leu Lys
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 30

Pro Val Leu Glu Leu Phe Lys Glu Leu Leu Gln Glu Leu Leu Glu Ala
1               5                   10                  15

Leu Lys Gln Lys Leu Lys
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 31

Gly Val Leu Asp Leu Phe Arg Glu Leu Leu Asn Glu Leu Leu Glu Ala
1               5                   10                  15

Leu Lys Gln Lys Leu Lys
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 32

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide
```

-continued

```
<400> SEQUENCE: 33

Pro Val Leu Asp Leu Phe Arg Glu Gly Leu Asn Glu Leu Leu Glu Ala
1               5                   10                  15

Leu Lys Gln Lys Leu Lys
            20

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 34

Pro Val Leu Asp Leu Phe Arg Glu Leu Leu Asn Glu Leu Leu Glu Gly
1               5                   10                  15

Leu Lys Gln Lys Leu Lys
            20

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 35

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 36

Pro Val Leu Asp Leu Phe Arg Glu Leu Leu Asn Glu Leu Leu Glu Ala
1               5                   10                  15

Leu Gln Lys Lys Leu Lys
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 37

Pro Val Leu Asp Phe Phe Arg Glu Leu Leu Asn Glu Leu Glu Ala Leu
1               5                   10                  15

Lys Gln Lys Leu Lys
            20

<210> SEQ ID NO 38
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      amphipathic peptide

<400> SEQUENCE: 38

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 39

Gly Val Leu Glu Leu Phe Glu Asn Leu Leu Glu Arg Leu Leu Asp Ala
1               5                   10                  15

Leu Gln Lys Lys Leu Lys
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 40

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 41

Pro Val Leu Glu Leu Phe Glu Asn Leu Leu Glu Arg Leu Phe Asp Ala
1               5                   10                  15

Leu Gln Lys Lys Leu Lys
            20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 42

Pro Val Leu Glu Leu Phe Glu Asn Leu Leu Glu Arg Leu Gly Asp Ala
1               5                   10                  15

Leu Gln Lys Lys Leu Lys
            20
```

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 43

Pro Val Leu Glu Leu Phe Glu Asn Leu Trp Glu Arg Leu Leu Asp Ala
1               5                   10                  15

Leu Gln Lys Lys Leu Lys
            20

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 44

Pro Leu Leu Glu Leu Phe Glu Asn Leu Leu Glu Arg Leu Leu Asp Ala
1               5                   10                  15

Leu Gln Lys Lys Leu Lys
            20

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 45

Pro Val Leu Glu Leu Phe Glu Asn Leu Gly Glu Arg Leu Leu Asp Ala
1               5                   10                  15

Leu Gln Lys Lys Leu Lys
            20

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      amphipathic peptide

<400> SEQUENCE: 46

Pro Val Phe Glu Leu Phe Glu Asn Leu Leu Glu Arg Leu Leu Asp Ala
1               5                   10                  15

Leu Gln Lys Lys Leu Lys
            20

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:

<223> OTHER INFORMATION: C-term amidated

<400> SEQUENCE: 47

Pro Val Leu Asp Leu Leu Arg Glu Leu Leu Glu Glu Leu Lys Gln Lys
1               5                   10                  15

Leu Lys

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 48

Pro Val Leu Asp Leu Phe Lys Glu Leu Leu Glu Glu Leu Lys Gln Lys
1               5                   10                  15

Leu Lys

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 49

Pro Val Leu Asp Leu Phe Arg Glu Leu Leu Glu Glu Leu Lys Gln Lys
1               5                   10                  15

Leu Lys

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 50

Pro Val Leu Glu Leu Phe Arg Glu Leu Leu Glu Glu Leu Lys Gln Lys
1               5                   10                  15

Leu Lys

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:

```
<223> OTHER INFORMATION: C-term amidated

<400> SEQUENCE: 51

Pro Val Leu Glu Leu Phe Lys Glu Leu Leu Glu Glu Leu Lys Gln Lys
1               5                   10                  15

Leu Lys

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 52

Pro Val Leu Asp Leu Phe Arg Glu Leu Leu Glu Glu Leu Lys Asn Lys
1               5                   10                  15

Leu Lys

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 53

Pro Leu Leu Asp Leu Phe Arg Glu Leu Leu Glu Glu Leu Lys Gln Lys
1               5                   10                  15

Leu Lys

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 54

Gly Val Leu Asp Leu Phe Arg Glu Leu Leu Glu Glu Leu Lys Gln Lys
1               5                   10                  15

Leu Lys

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
```

<223> OTHER INFORMATION: C-term amidated

<400> SEQUENCE: 55

Pro Val Leu Asp Leu Phe Arg Glu Leu Trp Glu Glu Leu Lys Gln Lys
1               5                   10                  15

Leu Lys

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 56

Asn Val Leu Asp Leu Phe Arg Glu Leu Leu Glu Glu Leu Lys Gln Lys
1               5                   10                  15

Leu Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 57

Pro Leu Leu Asp Leu Phe Lys Glu Leu Leu Glu Glu Leu Lys Gln Lys
1               5                   10                  15

Leu Lys

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 58

Pro Ala Leu Glu Leu Phe Lys Asp Leu Leu Glu Glu Leu Arg Gln Lys
1               5                   10                  15

Leu Arg

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:

<223> OTHER INFORMATION: C-term amidated

<400> SEQUENCE: 59

Ala Val Leu Asp Leu Phe Arg Glu Leu Leu Glu Glu Leu Lys Gln Lys
1               5                   10                  15

Leu Lys

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 60

Pro Val Leu Asp Phe Phe Arg Glu Leu Leu Glu Glu Leu Lys Gln Lys
1               5                   10                  15

Leu Lys

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 61

Pro Val Leu Asp Leu Phe Arg Glu Trp Leu Glu Glu Leu Lys Gln Lys
1               5                   10                  15

Leu Lys

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:
<223> OTHER INFORMATION: C-term amidated

<400> SEQUENCE: 62

Pro Leu Leu Glu Leu Leu Lys Glu Leu Leu Glu Glu Leu Lys Gln Lys
1               5                   10                  15

Leu Lys

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      amphipathic peptide
<220> FEATURE:
<223> OTHER INFORMATION: N-term acetylated
<220> FEATURE:

```
<223> OTHER INFORMATION: C-term amidated

<400> SEQUENCE: 63

Pro Val Leu Glu Leu Leu Lys Glu Leu Leu Glu Glu Leu Lys Gln Lys
1               5                   10                  15

Leu Lys
```

DETECTION OF LCAT ACTIVITY

CROSS-REFERENCE TO RELATED APPLICATIONS

This application is a U.S. National Stage application of International Application No. PCT/US2011/067571, filed on Dec. 28, 2011, said International Application No. PCT/US2011/067571 claims benefit under 35 U.S.C. §119(e) of the U.S. Provisional Application No. 61/428,925, filed on Dec. 31, 2010. Each of the above listed applications is incorporated by reference herein in its entirety for all purposes.

REFERENCE TO THE SEQUENCE LISTING

This application incorporates by reference a Sequence Listing submitted with this application as text filed entitled LCAT-130US1 SL.txt, created on Sep. 5, 2013, and having a size of 23,309 bytes.

FIELD

The present disclosure relates to methods for detecting and measuring lecithin:cholesterol acyltransferase (LCAT) activity in solution, methods for identification of LCAT modulating agents, and kits used to carry out the methods.

BACKGROUND

The enzyme lecithin-cholesterol acyltransferase (LCAT) circulates in the plasma portion of blood in association with high-density lipoproteins (HDL). LCAT catalyzes the hydrolysis of fatty acids from phosphatidylcholine (PC) within HDL and subsequently transfers most of that fatty acid to an ester bond with cholesterol within the same HDL to form cholesteryl ester (FIG. 1). A smaller portion of the fatty acid removed from PC may be released to water as free fatty acid. Of the two fatty acyl chains in PC, the fatty acid at the sn-2 position of the glycerol backbone in PC is the principle target of LCAT although the fatty acid esterified at the sn-1 position can also be hydrolyzed.

Apolipoprotein AI (apoA-I), which is the major protein component of HDL, is an essential cofactor for activation of LCAT. A matrix of PC and cholesterol alone, without apoA-I or similar activator, reacts slowly with LCAT. Other LCAT activity-enhancers, in addition to apoA-I, are known. These include the apolipoproteins E, A-IV and C-I. Synthetic peptides capable of activating LCAT in the same manner as apoA-I have also been described.

Cholesterol is the natural and, likely, most active substrate for LCAT but other sterols are known to be substrates for esterification by LCAT. The other sterols include phytosterols, steroid hormones such as estradiol, and fungal sterols.

The enzymatic activity of LCAT in plasma is essential for maintaining good health. Persons with the genetic disease familial LCAT deficiency (FLD) lack functional LCAT in their blood and, as a result, develop corneal opacities, anemia, and kidney disease which inevitably leads to kidney failure before the fourth decade of their life. A milder form of LCAT deficiency also occurs and is known as fish eye disease (FED) in which corneal opacity is the only clinical symptom. There is also evidence of an increased risk of vascular disease in FED. Both FLD and FED result from mutations in the LCAT gene.

Diminished plasma LCAT activity is also associated with increased illness in persons with a normal LCAT gene. For example, plasma LCAT activity is lower than normal in persons with chronic kidney disease, in those suffering cardiovascular disease, in liver disease, during sepsis, and in rheumatic disease patients.

Understanding and diagnosing the links between health and proper LCAT function as well as assessing the benefit of current therapies and the development of new therapies is dependent on reliable and facile methods for measuring LCAT activity.

A variety of assay protocols have been described for measurement of LCAT activity. They vary, in part, according to the particular LCAT enzymatic chemistry to be assayed, since there are two principle reactions catalyzed by LCAT. Cholesterol esterification by transacylation of fatty acid from phosphatidylcholine to cholesterol to form cholesteryl ester is the principal activity of LCAT and, correspondingly, the most broadly assayed. Many assay protocols are described and a commercial kit is available for measuring cholesterol esterification Water can also serve as an acyl-chain acceptor in the transacylation reaction, in which case phospholipid hydrolysis is the enzymatic activity measured. Assay procedures and kits have been described that measure the hydrolytic deacylation of phospholipids by LCAT. A third, but far less common type of LCAT assay, measures the LCAT-dependent transacylation of a fatty acid moiety from phosphatidylcholine to lysophosphatidylcholine.

Most cholesterol esterification assays use radiolabeled cholesterol incorporated into an appropriate substrate matrix, typically a phosphatidylcholine and cholesterol mixture complexed with apoA-I, and measure the appearance of radioactive cholesteryl ester due to LCAT. The substrate complex is usually formed by combination of the individual substrate components but the use of radiolabeled cholesterol incorporated into natural plasma lipoproteins in plasma or serum has also been described. Some have described procedures to enhance the detection of LCAT activity with plasma HDL, the target substrate of LCAT, by first removing non-HDL lipoproteins from plasma or serum before the addition of radiolabeled cholesterol and subsequent measurement of radiolabeled cholesteryl ester formation.

In lieu of radioactivity, some cholesterol esterification assays are based on the direct measurement of cholesterol depletion due to esterification for example, by cholesterol mass detection techniques (e.g. gas chromatography) or enzyme-based colorimetric assays of cholesterol.

Some assay methods for detecting LCAT activity are designed to detect the deacylation of phosphatidylcholine alone, in the absence of cholesterol. These assay methods either use radiolabeled phosphatidylcholine substrate in which the appearance of radiolabeled fatty acid or lysophosphatidylcholine is detected, or they use a phosphatidylcholine analog containing a fluorescent moiety that can be monitored for changes in spectral properties as a result of phosphatidylcholine deacylation by LCAT.

Two types of kits for the assay of LCAT are available for purchase from vendors, but none functions in the manner of the assay presented herein. One of the available kits is based on detection of phosphatidylcholine hydrolysis by monitoring fluorescence changes in a fluorescent PC analog as a result of LCAT activity (Roar Biomedical, Inc., New York, N.Y.). The second type of kit uses an enzyme-based colorimetric assay of cholesterol to detect the decline in free cholesterol in a cholesterol:phosphatidylcholine complex as a result of cholesterol esterification by LCAT (Sekisui Medical Co., Ltd., Tokyo, Japan).

The primary and, thus, most relevant activity of LCAT to detect and measure by assay is the transacylation of fatty acid from PC to cholesterol to form cholesteryl ester. FIG. 1 depicts the LCAT reaction in which LCAT catalyzes the transacylation of the fatty acyl group from the sn-2 position in the glycerol backbone of phosphatidylcholine to cholesterol. The products of the reaction are lysophosphatidylcholine and cholesteryl ester.

The most sensitive and most widely used LCAT assay procedures are based on the detection of radiolabeled cholesteryl ester formation from radiolabeled substrates. While the radiolabel-based assays are popular they are also cumbersome and lengthy due to the need to employ lipid extraction and chromatography steps to enable resolution of radiolabeled substrate and product for quantitation.

Measurement of LCAT activity is greatly simplified when, rather than analyzing radiolabeled products, enzymatic assay of unesterified cholesterol before and after reaction with LCAT is used to deduce the change in free cholesterol which relates directly to the amount of CE product formed. The enzymatic assay of cholesterol is much more efficient since extraction and separation of cholesterol and CE product is not necessary. Despite this advantage over the radiolabel method, the shortcoming of the enzymatic method is that it is much less sensitive and, thus, prone to greater error in detection of low levels of LCAT or of small changes in LCAT activity. There is a need for an LCAT assay procedure that overcomes these various shortcomings.

SUMMARY

The present disclosure provides methods for determining the activity of LCAT in a sample and methods for identifying LCAT activating agents. The methods of the invention detect and quantitate the sterol esterification activity of LCAT. The present disclosure provides for methods that use a fluorescent sterol as a substrate for esterification by LCAT followed by the use of a sterol oxidase (e.g. COx) to convert non-esterified sterol to a non-fluorescent product so that the esterified sterol is the only fluorescent entity remaining to be quantitated by fluorescence measurement. The disclosed methods enable the accurate determination of the amount of steroyl ester formed by direct measurement of steroyl ester fluorescence without interference from fluorescence of non-esterified sterol, thereby enabling detection of LCAT activity level in the sample.

One aspect of the present disclosure relates to methods of determining the level of LCAT activity in an assay sample comprising: providing a synthetic substrate comprising: a phospholipid, a fluorescent sterol, and an LCAT activity-enhancer; contacting the synthetic substrate with the assay sample to yield an assay mixture; incubating the assay mixture for a period of time; adding a COx enzyme to the assay mixture; and determining the LCAT activity in the sample.

Another aspect of the present disclosure relates to methods of identifying an LCAT activating agent comprising: providing a synthetic substrate comprising: a phospholipid; a fluorescent sterol; and an LCAT activity-enhancer; contacting the synthetic substrate with a test agent or a control vehicle to yield an assay mixture; adding LCAT to the assay mixture to yield a reaction mixture; incubating the reaction mixture; adding a COx enzyme to the reaction mixture; determining the activity of LCAT in the sample; and comparing the activity of LCAT in the presence of the test agent, to the activity with the activity of LCAT in the absence of test agent, wherein a test agent is an LCAT activating agent when the activity of LCAT in the presence of test agent is greater than the activity of LCAT in the absence of the test agent.

BRIEF DESCRIPTION OF THE FIGURES

FIG. 7 is a graph showing the attenuation of measured LCAT activity in a plasma sample due to the presence non-HDL lipoproteins (Untreated) compared to a plasma sample from which the non-HDL lipoproteins have been precipitated (Precipitated).

DETAILED DESCRIPTION

Definitions and Abbreviations

Figure 1:
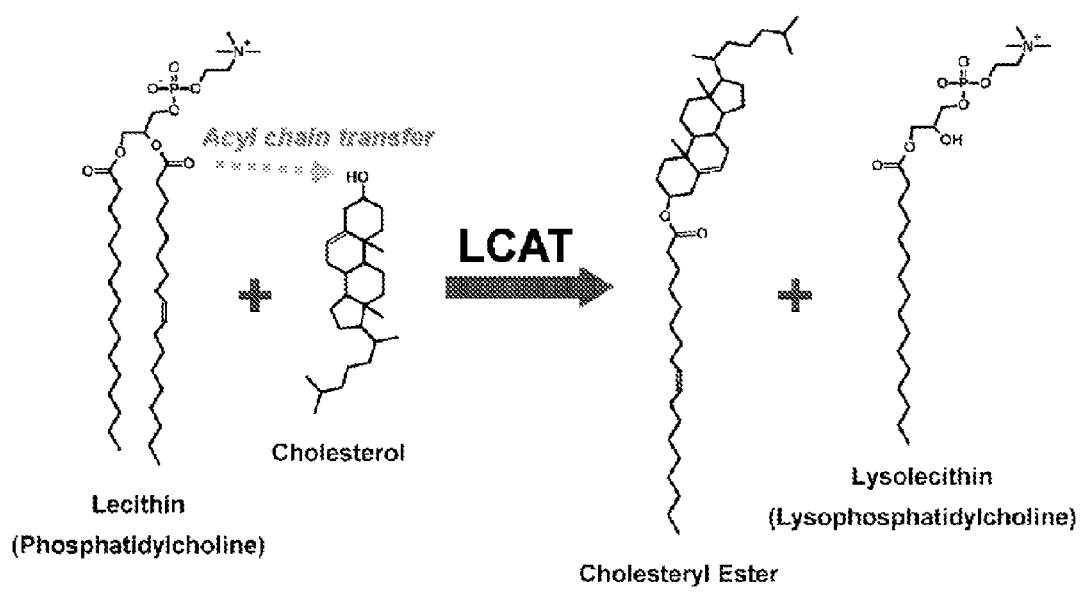
FIG. 1 depicts the LCAT reaction in which LCAT catalyzes the transacylation of the fatty acyl group from the sn-2 position in the glycerol backbone of phosphatidylcholine to cholesterol to form the reaction products, lysophosphatidylcholine and cholesteryl ester.

COx is an abbreviation for Cholesterol oxidase.

DHE is an abbreviation for Dehydroergosterol, Ergosta-5,7,9(11),22-tetraen-3β-ol.

ApoA-I is an abbreviation of Apolipoprotein A-I and these terms are used interchangeably herein. As used herein, the term apoA-I includes wild-type apoA-I as well as sequence variants, which retain at least one apoA-I activity. For example apoA-I includes, but is not limited to, apoA-I isolated from human as well as non-human mammalian plasma, man-made apoA-I variants, and naturally occurring genetic variants such as apoA-I (Milano), apoA-1 (Paris), and apoA-1 (Oslo).

HDL is an abbreviation for high-density lipoprotein.

POPC is an abbreviation for 1-Palmitoyl-2-oleoyl-sn-glycero-3-phosphocholine.

PL is an abbreviation for phospholipid.

PC is an abbreviation for phosphatidylcholine.

LCAT is an abbreviation for lecithin:cholesterol acyltransferase. Preferably the LCAT used in the methods of the present disclosure is recombinantly produced human LCAT (using mammalian cells, insect cells or plants as a recombinant protein expression system) although the LCAT may be obtained by any suitable methods e.g., isolation from human plasma.

LCAT activity-enhancer means any chemical entity that increases the rate at which LCAT esterifies sterol in a mixture of phospholipid and sterol. For example, apolipoprotein A-1 and LCAT-activating peptides are LCAT activity enhancers.

LCAT-activating peptide means an amphipathic peptide having from 18 to 40 amino acids which activates LCAT. LAP is an abbreviation for LCAT-activating peptide.

A test agent, as used herein, means any chemical entity, e.g. a small molecule, or a biologic molecule to be tested for LCAT activity using an assay according to the present disclosure. Biologic molecules, include but are not limited to, polypeptides and nucleic acids.

rhLCAT is an abbreviation for recombinant human LCAT.

rHDL or reconstituted HDL as used herein, means a complex of apolipoprotein A-I, phospholipid, and a sterol substrate of LCAT. Suitable phospholipids include, but are not limited to, phosphatidylcholine, sphingomyelin, phosphatidylethanolamine, dimethylphosphatidylethanolamine, phosphatidylserine, phosphatidylinositol, phosphatidylglycerol, cardiolipin or mixtures thereof. Preferably the apolipoprotein A-I is recombinantly produced.

mHDL or mimetic HDL as used herein, means a complex of one or more LCAT-activating peptides; phospholipid; and a sterol substrate of LCAT. Suitable phospholipids include, but are not limited to, phosphatidylcholine, sphingomyelin, phosphatidylethanolamine, dimethylphosphatidylethanolamine, phosphatidylserine, phosphatidylinositol, phosphatidylglycerol, cardiolipin or mixtures thereof.

As used herein, the singular forms "a", "an", and "the" include plural references unless the context clearly dictates otherwise. Thus, for example, reference to "a phospholipid" is a reference to one or a plurality of phospholipids.

One aspect of the present invention relates to methods of determining the level of LCAT activity in an assay sample. One embodiment is a method of determining the level of LCAT activity in an assay sample comprising: a) providing a synthetic substrate comprising: 1) a phospholipid, 2) a fluorescent sterol, and 3) an LCAT activity-enhancer; b) contacting the synthetic substrate with the assay sample to yield an assay mixture; c) incubating the assay mixture for a period of time; d) adding a COx enzyme to the assay mixture; e) measuring the fluorescence level of the assay mixture; and f) determining the LCAT activity in the sample. The assay sample may, for example, be a preparation of LCAT, cell culture medium, aliquots from chromatographic separations, plasma, serum, or cerebrospinal fluid.

The methods of the present invention are useful, for example, for the determination of LCAT levels in a subject's plasma or serum, for example to aid in the diagnosis of familial LCAT deficiency, of fish eye disease or other conditions of abnormal LCAT activity. In addition, the methods of the present invention are useful for monitoring patients LCAT activity during therapy, following administration of drugs, including administration of LCAT. Further the methods of the present invention are useful for monitoring LCAT activity in serum or plasma from non-human species or assessing the activity of recombinant LCAT from different preparations, in particular between different lots of recombinantly produced LCAT to allow standardization.

Another aspect of the present invention relates to methods of identifying an LCAT activating agent. One embodiment is a method of identifying an LCAT activating agent comprising: a) providing a synthetic substrate comprising: 1) a phospholipid; 2) a fluorescent sterol; and 3) an LCAT activity-enhancer; b) contacting the synthetic substrate with a test agent or a control vehicle to yield an assay mixture; c) adding LCAT to the assay mixture to yield a reaction mixture; d) incubating the reaction mixture; e) adding a COx enzyme to the reaction mixture; f) measuring the fluorescence level of the sample; g) determining the activity of LCAT in the assay mixture; and h) comparing the activity of LCAT in the presence of the test agent, to the activity with the activity of LCAT in the absence of test agent, wherein a test agent is an LCAT activating agent when the activity of LCAT in the presence of test agent is greater than the activity of LCAT in the absence of the test agent.

Another aspect of the present invention relates to methods of identifying an LCAT inhibitory agent. One embodiment is a method of identifying an LCAT inhibitory agent comprising: a) providing a synthetic substrate comprising: 1) a phospholipid; 2) a fluorescent sterol; and 3) an LCAT activity-enhancer; b) contacting the synthetic substrate with a test agent or a control vehicle to yield an assay mixture; c) adding LCAT to the assay mixture to yield a reaction mixture; d) incubating the reaction mixture; e) adding a COx enzyme to the reaction mixture; f) measuring the fluorescence level of the sample; g) determining the activity of LCAT in the assay mixture; and h) comparing the activity of LCAT in the presence of the test agent, to the activity with the activity of LCAT in the absence of test agent, wherein a test agent is an LCAT inhibitory agent when the activity of LCAT in the presence of test agent is less than the activity of LCAT in the absence of the test agent.

The methods of the present disclosure are generally carried out using multi-well assay plates, e.g. 24-well, 96-well, 384-well plates, as such the methods of the present disclosure are well suited for use in high-throughput screening. Fluorescence may be measured by any suitable technique; such techniques are well known in the art. For example, an assay plate maybe scanned in a fluorescence plate reader which is set at suitable excitation and emission wavelengths for the fluorescent sterol. The particular wavelengths chosen may vary depending on the particular fluorescent sterol used. In addition, the wavelengths may be varied to provide optimal signal to noise ratio, dependent on the model of the plate reader used. For example, suitable wavelengths for use when the sterol is DHE may be approximately 325 nm (excitation) and 395 nm (emission).

LCAT activity is generally expressed as the amount of steryl ester formed per unit time per unit LCAT mass (e.g. nmol/µg/hr). The amount of steryl ester product formed in a test well may be calculated from the net fluorescence of test wells (test fluorescence—blank fluorescence) divided by the net fluorescence of the control wells (control fluorescence—blank fluorescence) times the DHE content of the control wells. In this calculation, test wells comprise LCAT substrate and a sample, the blank wells and control wells receive no sample. After incubation, COx is added in a solution of buffer and detergent to the test wells and blank wells. The control wells receive only the solution of buffer with detergent without COx. The blank provides the background level of fluorescence and the control well provides the maximum fluorescence of the fluorescent sterol.

Fluorescent sterols suitable for use in the methods of the present invention include, but are not limited to, analogs of cholesterol having a 5,7,9-triene ring system, for example dehydroergosterol (DHE) (ergosta-5,7,9(11),22-tetraen-3β-ol) or cholestatrienol (cholesta-5,7,9(11)-trien-3β-ol) or other similar sterols containing a similar conjugated polyene system.

The selective elimination of fluorescence from non-esterified sterol by COx treatment is possible for two reasons. First, in order for a sterol to be oxidized by COx, the sterol must have a free 3-β-hydroxyl group. Esterification of the 3-β-hydroxyl by LCAT protects sterol from oxidation by COx. Second, COx oxidation of any unesterified sterol substrate with a 5,7,9-triene system results in a rearrangement of the electrons in the fluorescent conjugated 5,7,9-triene system thereby rendering the oxidized product non-fluorescent.

Hence, only esterified sterol will be protected from oxidation and remain fluorescent after COx addition.

One skilled in the art will recognize that certain fluorescent sterols are not suitable for use in the methods of the present invention. For example, fluorescent sterols in which the fluorophore is located in a position isolated from the site of COx oxidation as in NBD-cholesterol (22-(N-(7-nitrobenz-2-oxa-1,3-diazol-4-yl)amino)-23,24-bisnor-5-cholen-3β-ol) which is known to be a substrate for LCAT but has the fluorophore located in the alkyl side-chain.

Figure 2:
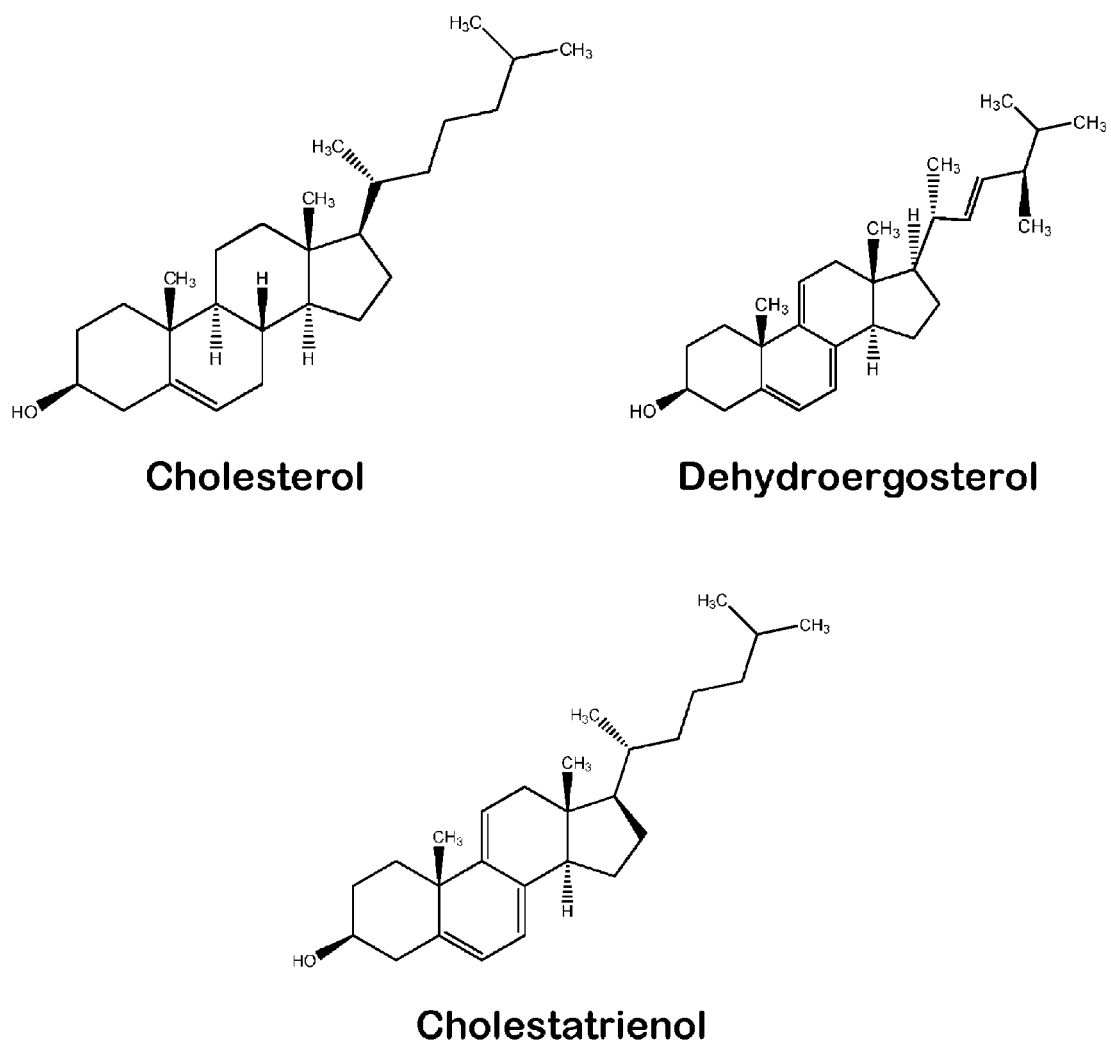
FIG. 2 shows the structures of cholesterol and the fluorescent analogs dehydroergosterol and cholestatrienol.

In one embodiment the fluorescent sterol is an analog of cholesterol having a 5,7,9-triene ring system. In certain embodiments the fluorescent sterol is DHE. In another embodiment the fluorescent sterol is cholestatrienol. DHE and cholestatrienol are close structural analogs of cholesterol (as shown in FIG. 2) and are substrates for the LCAT esterification reaction. DHE and cholestatrienol exhibit intrinsic fluorescence which enables highly sensitive detection of the substrate and the substrate ester product. For example, DHE and the DHE ester product. The present invention allows for substrate and product resolution by selective conversion of an unesterified fluorescent sterol to a non-fluorescent product by means of cholesterol oxidase (COx), directly, in the original reaction solution, without the need for extractions or chromatography. Analysis of the fluorescence remaining after COx treatment yields a direct measure of the amount of substrate ester product. For example, when DHE is the substrate the measurement of fluorescence after COx treatment is a direct measure of the amount of DHE ester (DE) formed.

It is contemplated that in any of the embodiments of the present invention that any one or a combination of Phospholipids may be used. Phospholipids suitable for the presently disclosed methods include, but are not limited to, phosphatidylcholine, sphingomyelin, phosphatidylserine, phosphatidylethanolamine, dimethylphosphatidylethanolamine, phosphatidyinositol, phosphatidylglycerol, cardiolipin and mixtures thereof. Exemplary phospholipids include, but are not limited to, egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof. In a preferred embodiment the phospholipid is 1-Palmitoyl-2-oleoyl-sn-glycero-3-phosphocholine.

COx enzymes suitable for the presently disclosed methods include, but are not limited to, those derived from bacteria. Bacterial COx enzymes include those isolated from *Streptomyces* sp., *Cellulomonas* sp., *Rhodococcus equi*, *Vibrio harveyi*, *Salinispoara arenicola*, *Nostoc punctiforme*, *Frankia* sp., *Mycobacterium tuberculosis*, *Mycobacterium leprae*, *Corynebacterium urealyticum*, *Streptomyces coelicolor*, *Brevibacterium* sp., *Burkholderia cepacia*, *Burkholderia thailandensis*, *Pseudomonas fluorescens*, *Nocardia erythropolis*, *Chromobacterium* sp., and *Rhodococcus erythropolis*. Additionally, recombinantly produced COx enzymes are suitable for use in the presently disclosed methods. Various methods of production of recombinant proteins are well known in the art, for example using protein expression techniques in bacterial, fungal, insect or mammalian cells. Also suitable for use are genetically-modified COx enzymes in which one or more amino acid substitutions, amino acid additions or amino acid deletions have been incorporated by molecular biological methods and which retain or have enhanced 3-β-hydroxyl oxidation activity. The amino acid substitutions are generally conservative substitutions. Examples of conservative substitutions are shown in Table 2 below. Furthermore COx enzymes that have been chemically modified, such as by linkage of polyethylene glycol groups or by immobilization to surfaces, that retain or have enhanced 3-β-hydroxyl oxidation activity are suitable for the presently disclosed methods.

TABLE 2

| Original Residue | Exemplary Conservative Substitutions |
|---|---|
| A | G, S |
| R | K |
| N | Q, H |
| D | E |
| C | S |
| Q | N |
| E | D |
| G | A, P |
| H | N, Q |
| I | L, V |
| L | I, V |
| K | R, Q, E |
| M | L, Y, I |
| F | M, L, Y |
| S | T |
| T | S |
| W | Y |
| Tyr | W, F |
| Val | I, L |

The LCAT reaction is dependent on the form in which substrates are presented to LCAT. In the presently disclosed methods, synthetic substrates are used. LCAT activity is enhanced when apoA-I is combined with the fluorescent sterol and phospholipid to form rHDL (Jonas, (1986) J. Lipid Res. 27: 689-698). Thus, in some embodiments the synthetic substrate is in the form of rHDL. Suitable phospholipids for forming rHDL include, but are not limited to, phosphatidylcholine, sphingomyelin, phosphatidylethanolamine, dimethylphosphatidylethanol-amine, phosphatidylserine, phosphatidyinositol, phosphatidylglycerol, cardiolipin and mixtures thereof. Thus, in one embodiment the rHDL comprises phosphatidylcholine. In another embodiment the rHDL comprises sphingomyelin. In another embodiment the rHDL comprises phosphatidylethanolamine. In another embodiment the rHDL comprises phosphatidylserine. In another embodiment the rHDL comprises phosphatidyinositol. In another embodiment the rHDL comprises phosphatidylglycerol. In another embodiment the rHDL comprises cardiolipin. In preferred embodiments the rHDL comprises DHE and phosphatidylcholine. In yet another preferred embodiment the rHDL comprises cholestatrienol and phosphatidylcholine.

In some embodiments the LCAT activity enhancer is a peptide having 16 to 45 amino acids that mimics the lipid binding and LCAT activating properties of apoA-I (an "LCAT-activating peptide"). This mixture of phospholipid, fluorescent sterol and peptide is referred to herein as mHDL. LCAT-activating peptides are amphipathic peptides having from 16 to 45 amino acids which activate LCAT. For example, the peptides may be, for example, from 16 to 45, or 15 to 40, or 25 to 30, or 18-40, or 18-30, or 18 to 22 amino acids in length. These peptides can be unaltered or may be modified, for example by acetylation of the N-terminus or amidation of the C-terminus. Preferably the peptide is capable of forming a stable emulsion with phospholipid and a sterol.

The distinguishing feature of an amphipathic peptide is the arrangement of the amino acids in the peptide such that, in an alpha-helical conformation of the peptide, the more hydrophobic amino acid residues are congregated to one side of the helix while the more polar amino acids are located on the direct opposite face of the helix. Amphipathic peptides are defined by two measures. The first is mean hydrophobicity, which quantifies the average hydrophobicity for all amino acid residues in the peptide. The second is a measure of amphilicity known as the mean hydrophobic moment, which defines the degree of segregation of polar and nonpolar amino acid residues to opposing sides of the peptide helix (Pownall et al., 1983, FEBS 159(1,2):17-23). The calculated values for mean hydrophobicity and hydrophobic moment are dependent on the hydrophobicity values selected for each amino acid residue. Several lists of amino acid hydrophobicities have been published. Values used in the present disclosure are based on the amino acid hydrophobicity list as disclosed in Hessa et al. 2005, Nature 433:377-381. As used herein, an amphipathic peptide has a mean hydrophobicity greater than −1.5 and a mean hydrophobic moment greater than 0.6.

A variety of amphipathic peptides have been described that form stable micelle structures with phospholipid and cholesterol. However, not all such complexes will react effectively with LCAT. One skilled in the art can identify amphipathic peptides with suitable specific amino acid sequences. Amphipathic peptides suitable for use in producing mHDL include, but are not limited to those disclosed in U.S. Pat. Nos. 6,004,925, 6,046,166, 6,376,464, 6,602,854, 7,273,848, 7,307,058, D4F (Song et. al, (2009) Int J Biol Sci 5:637-646), L37pA (Alexander V. Bocharov et al. (2004) J. Biol. Chem. 279: 36072-36082), and peptides disclosed in D. Busseuil et al. (2008) Br J Pharmacol. 154(4): 765-773. Each of these references are hereby incorporated by reference. Exemplary peptides are provided in Table 1.

TABLE 1

| SEQ ID NO: | AMINO ACID SEQUENCE |
|---|---|
| 1 | P V L D L F R E L L N E L L E A L K Q K L K |
| 2 | P T L D L F R E L L N E L L E A L K Q K L K |
| 3 | P S L D L F R E L L N E L L E A L K Q K L K |
| 4 | P V L D L F R E L L N E L L Q K L K K |
| 5 | P T L D L F R E L L N E L L Q K L K K |
| 6 | P V L D L F R E L L E E L L Q K L K K |
| 7 | Ac-P V L D L F K E L L E E L F Q K L K K-NH$_2$ |
| 9 | Ac-E W L K A F L E K V L E K L K E L F-NH$_2$ |
| 15 | P V L D L F R E L L N E L L E L K Q K L K |
| 16 | G V L D L F R E L L N E L L E A L K Q K L K K |
| 17 | P V L D L F R E L L N E L L E W L K Q K L K |
| 18 | P V L D L F R E L L N E L L E A L K Q K L K K |
| 19 | P V L D L F R E L L N E L E A L K Q K L K |
| 20 | P V L D L F K E L L N E L L E A L K Q K L K |
| 21 | P V L D L F R E L L N E G L E A L K Q K L K |
| 22 | P V L D L F R E L G N E L L E A L K Q K L K |
| 23 | P V L D L F R E L L N E L L E A K Q K L K |
| 24 | P V L D L F K E L L Q E L L E A L K Q K L K |
| 25 | P V L D L F R E L L N E L L E A G K Q K L K |
| 26 | G V L D L F R E L L N E G L E A L K Q K L K |
| 27 | P V L D L F R E L L N E L L E A L O Q O L O |
| 28 | P V L D L F R E L W N E L L E A L K Q K L K |
| 29 | P V L D L L R E L L N E L L E A L K Q K L K |
| 30 | P V L E L F K E L L Q E L L E A L K Q K L K |
| 31 | G V L D L F R E L L N E L L E A L K Q K L K |
| 32 | P V L D L F R E L L N E G L E A L K Q K L K |

TABLE 1-continued

| SEQ ID NO: | AMINO ACID SEQUENCE |
|---|---|
| 33 | P V L D L F R E G L N E L L E A L K Q K L K |
| 34 | P V L D L F R E L L N E L L E G L K Q K L K |
| 35 | P L L E L F K E L L Q E L L E A L K Q K L K |
| 36 | P V L D L F R E L L N E L L E A L Q K K L K |
| 37 | P V L D F F R E L L N E L E A L K Q K L K |
| 38 | P V L E L F E N L L E R L L D A L Q K K L K |
| 39 | G V L E L F E N L L E R L L D A L Q K K L K |
| 40 | P V L E L F E N L L E R L L D A L Q K K L K |
| 41 | P V L E L F E N L L E R L F D A L Q K K L K |
| 42 | P V L E L F E N L L E R L G D A L Q K K L K |
| 43 | P V L E L F E N L W E R L L D A L Q K K L K |
| 44 | P L L E L F E N L L E R L L D A L Q K K L K |
| 45 | P V L E L F E N L G E R L L D A L Q K K L K |
| 46 | P V F E L F E N L L E R L L D A L Q K K L K |
| 47 | Ac-P V L D L L R E L L E E L K Q K L K-NH$_2$ |
| 48 | Ac-P V L D L F K E L L E E L K Q K L K-NH$_2$ |
| 49 | Ac-P V L D L F R E L L E E L K Q K L K-NH$_2$ |
| 50 | Ac-P V L E L F R E L L E E L K Q K L K-NH$_2$ |
| 51 | Ac-P V L E L F K E L L E E L K Q K L K-NH$_2$ |
| 52 | Ac-P V L D L F R E L L E E L K N K L K-NH$_2$ |
| 53 | Ac-P L L D L F R E L L E E L K Q K L K-NH$_2$ |
| 54 | Ac-G V L D L F R E L L E E L K Q K L K-NH$_2$ |
| 55 | Ac-P V L D L F R E L W E E L K Q K L K-NH$_2$ |
| 56 | Ac-N V L D L F R E L L E E L K Q K L K-NH$_2$ |
| 57 | Ac-P L L D L F K E L L E E L K Q K L K-NH$_2$ |
| 58 | Ac-P A L E L F K D L L E E L R Q K L R-NH$_2$ |
| 59 | Ac-A V L D L F R E L L E E L K Q K L K-NH$_2$ |
| 60 | Ac-P V L D F F R E L L E E L K Q K L K-NH$_2$ |
| 61 | Ac-P V L D L F R E W L E E L K Q K L K-NH$_2$ |
| 62 | Ac-P L L E L L K E L L E E L K Q K L K-NH$_2$ |
| 63 | Ac-P V L E L L K E L L E E L K Q K L K-NH$_2$ |

SEQ ID NOs: 1, and 15-63 are disclosed in U.S. Pat. No. 7,273,848 Peptide terminal modifications are indicated by Ac- for acetylated N-terminus and by —NH$_2$ for amidated C-terminus In any of the embodiments of the present invention any one or a combination of LCAT-activating peptide may be used. LCAT-activating peptides include modified peptides. Such modifications include, but are not limited to N-terminal acylated or C-terminal amidated peptides. Exemplary peptides include peptides having the sequence provided by SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 9 or SEQ ID NO: 15, or SEQ ID NO: 16, or SEQ ID NO: 17, or SEQ ID NO: 18, or SEQ ID NO: 19, or SEQ ID NO: 20, or SEQ ID NO: 21, or SEQ ID NO: 22, or SEQ ID NO: 23, or SEQ ID NO: 24, or SEQ ID NO: 25, or SEQ ID NO: 26 or SEQ ID NO: 27, SEQ ID NO: 28, or SEQ ID NO: 29, or SEQ ID NO: 30, or SEQ ID NO: 31, or SEQ ID NO: 32, or SEQ ID NO: 33, or SEQ ID NO: 34, or SEQ ID NO: 35, or SEQ ID NO: 36, or SEQ ID NO: 37, or SEQ ID NO: 38, or SEQ ID NO: 39, or SEQ ID NO: 40, or SEQ ID NO: 41, or SEQ ID NO: 42, or SEQ ID NO: 43 or SEQ ID NO: 44, SEQ ID NO: 45, or SEQ ID NO: 46, or SEQ ID NO: 47, or SEQ ID NO: 48, or SEQ ID NO: 49, or SEQ ID NO: 50, or SEQ ID NO: 51, or SEQ ID NO: 52, or SEQ ID NO: 53, or SEQ ID NO: 54, or SEQ ID NO: 55, or SEQ ID NO: 56, or SEQ ID NO: 57, or SEQ ID NO: 58 or SEQ ID NO: 59 or SEQ ID NO: 60, SEQ ID NO: 61, or SEQ ID NO: 62, or SEQ ID NO: 63.

Suitable phospholipids for forming mHDL include, but are not limited to, phosphatidylcholine, sphingomyelin phosphatidylethanolamine, dimethylphosphatidylethanolamine, dimethylphosphatidylethanolamine, phosphatidylinositol, phosphatidylglycerol, cardiolipin and mixtures thereof. Thus, in one embodiment the mHDL comprises an LCAT-activating peptide or a combination of two or more types of LCAT-activating peptides and DHE and phosphatidylcholine. In another embodiment the mHDL comprises an LCAT-activating peptide, DHE, and sphingomyelin. In another embodiment the mHDL comprises an LCAT-activating peptide, DHE, and phosphatidylethanolamine. In another embodiment the mHDL comprises an LCAT-activating peptide, DHE, and phosphatidylserine. In another embodiment the mHDL comprises an LCAT-activating peptide, DHE, and phosphatidyinositol. In another embodiment the mHDL comprises an LCAT-activating peptide, DHE, and phosphatidylglycerol. In another embodiment the mHDL comprises an LCAT-activating peptide, DHE, and cardiolipin. In preferred embodiments the mHDL comprises an LCAT-activating peptide, DHE, and phosphatidylcholine.

Any embodiment of the invention comprising an LCAT-activating peptide may include the use of one, or any combination of LCAT-activating peptides.

In yet another embodiment the mHDL comprises an LCAT-activating peptide, cholestatrienol, and phosphatidylcholine. In another embodiment the mHDL comprises an LCAT-activating peptide, cholestatrienol, and sphingomyelin. In another embodiment the mHDL comprises an LCAT-activating peptide, cholestatrienol, and phosphatidylethanolamine. In another embodiment the mHDL comprises an LCAT-activating peptide, cholestatrienol, and phosphatidylserine. In another embodiment the mHDL comprises an LCAT-activating peptide, cholestatrienol, and phosphatidyinositol. In another embodiment the mHDL comprises an LCAT-activating peptide, cholestatrienol, and phosphatidylglycerol. In another embodiment the mHDL comprises an LCAT-activating peptide, cholestatrienol, and cardiolipin. In preferred embodiments the mHDL comprises an LCAT-activating peptide, cholestatrienol, and phosphatidylcholine. In yet another preferred embodiment the mHDL comprises cholestatrienol and phosphatidylcholine.

In certain embodiments the sample to be assayed is plasma or serum. Assays of samples containing plasma or serum are complicated by the presence of cholesterol in the endogenous lipoproteins. The endogenous cholesterol will compete with externally-added fluorescent sterols thereby reducing the rate of esterification of the fluorescent sterol by LCAT. One approach for addressing this competition is to increase the amount of fluorescent sterol in the assay mixture. In addition to the competition by endogenous cholesterol, a significant portion of externally-added fluorescent sterol may be distributed to apolipoprotein B-containing lipoproteins which are present in the plasma or serum but are significantly less reactive with LCAT than rHDL or mHDL. This redistribution may reduce the rate of esterification of the fluorescent sterol.

The effects of cholesterol competition and of the fluorescent sterol redistribution can be dampened by selective removal of apolipoprotein B lipoproteins, for example by precipitation from the sample to be assayed. Procedures for selective removal of apolipoprotein B lipoproteins from plasma or serum are known in the art (See Assmann et al. (1983) Clin. Chem. 29:2026-2030, and (P. S. Bachorik and J. J. Albers, (1986) Methods Enzymol. 129: 78-100). In a particular embodiment the sample is plasma. In another embodiment the sample is serum.

The methods of the present disclosure are also useful in the comparison and or standardization of LCAT preparations. For example, the LCAT activity of a batch of recombinantly produced LCAT can be measured and compared with the LCAT activity of a different batch.

In certain embodiments an antioxidant is included in the synthetic substrate to protect the fluorescent sterol from spontaneous oxidation. In certain embodiments, a lipophilic antioxidant is added to the mHDL or rHDL, i.e. after the mHDL or rHDL is formed. Suitable antioxidants include, but are not limited to, butylated hydroxytoluene, gallic acid esters or a tocopherol (e.g. vitamin E). Thus, in some embodiments the antioxidant is butylated hydroxytoluene. In some embodiments the antioxidant is a gallic acid ester. In some embodiments the antioxidant is a tocopherol. It is contemplated that any embodiment of the invention may include one or more antioxidant.

In certain embodiments a catalase enzyme is added with the COx in order to consume the hydrogen peroxide produced by the COx reaction and thereby protect the DHE esters or cholestatrienol from spontaneous oxidation.

In preferred embodiments, a detergent is added with the COx. Suitable detergents for use in the presently described assay include, but are not limited to, nonionic detergents such as Nonidet detergents, for example, Nonidet P40; Triton detergents, for example Triton X-100 or Triton X-114; Tween detergents, for example Tween 80 or Tween 20; polyoxyethylene octyl phenyl ether; or Brij, detergents, for example Brij-35. (Sigma-Aldrich, St. Louis, Mo.) It is contemplated that any embodiment of the invention comprising a detergent, may include the use of one or any combination of detergents. By non-limiting example, an embodiment may comprise Nonidet P40, or Triton X-100 or Triton X-114, or Tween 80 or Tween 20 or Brij-35 or polyoxyethylene octyl phenyl ether, or any combination thereof.

One embodiment is a method of determining the level of LCAT activity in an assay sample comprising: a) providing a synthetic substrate comprising: 1) a phospholipid, 2) a fluorescent sterol, and 3) an LCAT activity-enhancer; b) contacting the synthetic substrate with the assay sample to yield an assay mixture; c) incubating the assay mixture for a period of time; d) adding a COx enzyme to the assay mixture; e) measuring the fluorescence level of the assay mixture; and f) determining the LCAT activity in the sample, wherein the LCAT activity-enhancer, the phospholipid; and the fluorescent sterol are in the form of mHDL, the fluorescent sterol is a fluorescent sterol having a conjugated 5,7,9-triene system, the LCAT activity enhancer is an LCAT-activating peptide and the phospholipid is phosphatidylcholine; sphingomyelin, or phosphatidylethanolamine; or dimethylphosphatidylethanolamine; or phosphatidylserine; phosphatidyinositol; or phosphatidylglycerol; or cardiolipin, or a mixture thereof.

In another embodiment of a method of determining the level of LCAT activity, the LCAT activity-enhancer, the phospholipid; and the fluorescent sterol are in the form of mHDL, the fluorescent sterol is DHE, the LCAT activity enhancer is an LCAT-activating peptide and the phospholipid is phosphatidylcholine; sphingomyelin; phosphatidylethanolamine;

dimethylphosphatidylethanolamine; phosphatidylserine; phosphatidyinositol; phosphatidylglycerol; cardiolipin, or a mixture thereof.

In another embodiment of a method of determining the level of LCAT activity, the LCAT activity-enhancer, the phospholipid; and the fluorescent sterol are in the form of mHDL, the fluorescent sterol is DHE, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof. In a preferred embodiment the phospholipid is 1-Palmitoyl-2-oleoyl-sn-glycero-3-phosphocholine.

In another embodiment of a method of determining the level of LCAT activity the fluorescent sterol is DHE, the LCAT activity enhancer is a peptide having a sequence selected from Table 1, and the phospholipid is phosphatidylcholine; sphingomyelin; phosphatidylethanolamine; dimethylphosphatidylethanolamine; phosphatidylserine; phosphatidyinositol; phosphatidylglycerol; cardiolipin, or a mixture thereof.

In another embodiment of a method of determining the level of LCAT activity the fluorescent sterol is DHE, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9, and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of determining the level of LCAT activity, the LCAT activity-enhancer, the phospholipid; and the fluorescent sterol are in the form of mHDL, the fluorescent sterol is DHE, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of determining the level of LCAT activity the fluorescent sterol is DHE, the LCAT activity enhancer is an LCAT-activating peptide and the phospholipid is phosphatidylcholine. In another embodiment of a method of determining the level of LCAT activity, the fluorescent sterol is DHE, the LCAT activity enhancer is a peptide selected from Table 1, and the phospholipid is phosphatidylcholine.

In another embodiment of a method of determining the level of LCAT activity the fluorescent sterol is DHE, the LCAT activity enhancer is an LCAT-activating peptide and the phospholipid is phosphatidylcholine. In another embodiment of a method of determining the level of LCAT activity, the fluorescent sterol is DHE, the LCAT activity enhancer is a peptide selected from Table 1, and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of determining the level of LCAT activity, the LCAT activity-enhancer, the phospholipid; and the fluorescent sterol are in the form of mHDL, the fluorescent sterol is cholestatrienol, the LCAT activity enhancer is an LCAT-activating peptide and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of determining the level of LCAT activity, the LCAT activity-enhancer, the phospholipid; and the fluorescent sterol are in the form of mHDL, the fluorescent sterol is cholestatrienol, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of determining the level of LCAT activity, the fluorescent sterol is cholestatrienol, the LCAT activity enhancer is a peptide having a sequence selected from Table 1, and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of determining the level of LCAT activity, the fluorescent sterol is cholestatrienol, the LCAT activity enhancer is a peptide having the sequence of SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 9, and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of determining the level of LCAT activity, the LCAT activity-enhancer, the phospholipid; and the fluorescent sterol are in the form of mHDL, the fluorescent sterol is cholestatrienol, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof. In a particular embodiment the phospholipid is 1-Palmitoyl-2-oleoyl-sn-glycero-3-phosphocholine.

In another embodiment of a method of determining the level of LCAT activity the fluorescent sterol is cholestatrienol, the LCAT activity enhancer is an LCAT-activating peptide and the phospholipid is phosphatidylcholine. In another embodiment of a method of determining the level of LCAT activity the fluorescent sterol is DHE, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9, and the phospholipid is phosphatidylcholine, or the phospholipid is 1-Palmitoyl-2-oleoyl-sn-glycero-3-phosphocholine.

In another embodiment of a method of determining the level of LCAT activity the fluorescent sterol is cholestatrienol, the LCAT activity enhancer is an LCAT-activating peptide and the phospholipid is phosphatidylcholine. In another embodiment of a method of determining the level of LCAT activity the fluorescent sterol is DHE, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9, and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof. In a particular embodiment the phospholipid is 1-Palmitoyl-2-oleoyl-sn-glycero-3-phosphocholine.

Another embodiment is a method of determining the level of LCAT activity in an assay sample comprising: a) providing a synthetic substrate comprising: 1) a phospholipid, 2) a fluorescent sterol, and 3) an LCAT activity-enhancer; b) contacting the synthetic substrate with the assay sample to yield an assay mixture; c) incubating the assay mixture for a period of time; d) adding a COx enzyme to the assay mixture; e) measuring the fluorescence level of the assay mixture; and f) determining the LCAT activity in the sample, wherein step d) further comprises adding a detergent and wherein the LCAT activity-enhancer, the phospholipid; and the fluorescent sterol are in the form of mHDL, the fluorescent sterol is DHE or cholestatrienol, the LCAT activity enhancer is an LCAT-activating peptide.

Another embodiment is a method of determining the level of LCAT activity in an assay sample comprising: a) providing a synthetic substrate comprising: 1) a phospholipid, 2) a fluorescent sterol, 3) an LCAT activity-enhancer, and 4) a lipophilic antioxidant; b) contacting the synthetic substrate with the assay sample to yield an assay mixture; c) incubating the assay mixture for a period of time; d) adding a COx enzyme to the assay mixture; e) measuring the fluorescence of the assay mixture; and f) determining the LCAT activity in the sample, wherein step d) further comprises adding a detergent and wherein the LCAT activity-enhancer, the phospholipid; and the fluorescent sterol are in the form of mHDL, the fluorescent sterol is DHE or cholestatrienol, the LCAT activity enhancer is an LCAT-activating peptide.

Another embodiment is a method of determining the level of LCAT activity in an assay sample comprising: a) providing a synthetic substrate comprising: 1) a phospholipid, 2) a fluorescent sterol, 3) an LCAT activity-enhancer and 4) a lipophilic antioxidant; b) contacting the synthetic substrate with the assay sample to yield an assay mixture; c) incubating the assay mixture for a period of time; d) adding a COx enzyme to the assay mixture; e) measuring the fluorescence of the assay mixture; and f) determining the LCAT activity in the sample, wherein step d) further comprises adding a detergent, and a catalase and wherein the LCAT activity-enhancer, the phospholipid; and the fluorescent sterol are in the form of mHDL, the fluorescent sterol is DHE or cholestatrienol, the LCAT activity enhancer is an LCAT-activating peptide.

Another embodiment is a method of determining the level of LCAT activity in an assay sample comprising: a) providing a synthetic substrate comprising: 1) a phospholipid, 2) a fluorescent sterol, 3) an LCAT activity-enhancer, and 4) a lipophilic antioxidant; b) contacting the synthetic substrate with the assay sample to yield an assay mixture; c) incubating the assay mixture for a period of time; d) adding a COx enzyme to the assay mixture; e) measuring the fluorescence of the assay mixture; and f) determining the LCAT activity in the sample, wherein step d) further comprises adding a detergent, and a catalase and wherein the LCAT activity-enhancer, the phospholipid; and the fluorescent sterol are in the form of mHDL, the fluorescent sterol is DHE or cholestatrienol, the LCAT activity enhancer is an LCAT-activating peptide selected from Table 1.

Another embodiment is a method of determining the level of LCAT activity in an assay sample comprising: a) providing a synthetic substrate comprising: 1) a phospholipid, 2) a fluorescent sterol, and 3) an LCAT activity-enhancer and 4) a lipophilic antioxidant; b) contacting the synthetic substrate with the assay sample to yield an assay mixture; c) incubating the assay mixture for a period of time; d) adding a COx enzyme to the assay mixture; e) measuring the fluorescence of the assay mixture; and f) determining the LCAT activity in the sample wherein step d) further comprises adding a detergent, and a catalase and wherein the LCAT activity-enhancer, the phospholipid; and the fluorescent sterol are in the form of mHDL, the fluorescent sterol is DHE or cholestatrienol, the LCAT activity enhancer is a peptide having the sequence of SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 9 or SEQ ID NO: 15, or SEQ ID NO: 16, or SEQ ID NO: 17, or SEQ ID NO: 18, or SEQ ID NO: 19, or SEQ ID NO: 20, or SEQ ID NO: 21, or SEQ ID NO: 22, or SEQ ID NO: 23, or SEQ ID NO: 24, or SEQ ID NO: 25, or SEQ ID NO: 26 or SEQ ID NO: 27, SEQ ID NO: 28, or SEQ ID NO: 29, or SEQ ID NO: 30, or SEQ ID NO: 31, or SEQ ID NO: 32, or SEQ ID NO: 33, or SEQ ID NO: 34, or SEQ ID NO: 35, or SEQ ID NO: 36, or SEQ ID NO: 37, or SEQ ID NO: 38, or SEQ ID NO: 39, or SEQ ID NO: 40, or SEQ ID NO: 41, or SEQ ID NO: 42, or SEQ ID NO: 43 or SEQ ID NO: 44, SEQ ID NO: 45, or SEQ ID NO: 46, or SEQ ID NO: 47, or SEQ ID NO: 48, or SEQ ID NO: 49, or SEQ ID NO: 50, or SEQ ID NO: 51, or SEQ ID NO: 52, or SEQ ID NO: 53, or SEQ ID NO: 54, or SEQ ID NO: 55, or SEQ ID NO: 56, or SEQ ID NO: 57, or SEQ ID NO: 58 or SEQ ID NO: 59 or SEQ ID NO: 60, SEQ ID NO: 61, or SEQ ID NO: 62, or SEQ ID NO: 63. In another embodiment the peptide has the sequence of SEQ ID NO: 1. In another embodiment the peptide has the sequence of SEQ ID NO: 2. In another embodiment the peptide has the sequence of SEQ ID NO: 3. In another embodiment the peptide has the sequence of SEQ ID NO: 4. In another embodiment the peptide has the sequence of SEQ ID NO: 5. In another embodiment the peptide has the sequence of SEQ ID NO: 6. In another embodiment the peptide has the sequence of SEQ ID NO: 7. In another embodiment the peptide has the sequence of SEQ ID NO: 9.

Another aspect of the present invention relates to methods of identifying an LCAT activating agent. One embodiment is a method of identifying an LCAT activating agent comprising: a) providing a synthetic substrate comprising: 1) a phospholipid; 2) a fluorescent sterol; and 3) an LCAT activity-enhancer; b) contacting the synthetic substrate with a test agent or a control vehicle to yield an assay mixture; c) adding LCAT to the assay mixture to yield a reaction mixture; d) incubating the reaction mixture; e) adding a COx enzyme to the reaction mixture; f) measuring the fluorescence level of the sample; g) determining the activity of LCAT in the assay mixture; and h) comparing the activity of LCAT in the presence of the test agent, to the activity with the activity of LCAT in the absence of test agent, wherein a test agent is an LCAT activating agent when the activity of LCAT in the presence of test agent is greater than the activity of LCAT in the absence of the test agent.

In one embodiment of a method of identifying an LCAT activating agent, the LCAT activity-enhancer, the phospholipid; and the fluorescent sterol are in the form of mHDL, the fluorescent sterol is a fluorescent sterol having a conjugated 5,7,9-triene system, the LCAT activity enhancer is an LCAT-activating peptide and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of identifying an LCAT activating agent, the LCAT activity-enhancer, the phospholipid; and the fluorescent sterol are in the form of mHDL, the fluorescent sterol is DHE, the LCAT activity enhancer is an LCAT-activating peptide and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of identifying an LCAT activating agent, the LCAT activity-enhancer, the phospholipid; and the fluorescent sterol are in the form of mHDL, the fluorescent sterol is DHE, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of identifying an LCAT activating agent, the fluorescent sterol is DHE, the LCAT activity enhancer is a peptide having a sequence selected from Table 1, and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of identifying an LCAT activating agent, the fluorescent sterol is DHE, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9, and the phospholipid is phosphatidylcholine; sphingomyelin phosphatidylethanolamine; dimethylphosphatidylethanolamine; phosphatidylserine; phosphatidyinositol; phosphatidylglycerol; cardiolipin, or a mixture thereof.

In another embodiment of a method of identifying an LCAT activating agent, the LCAT activity-enhancer, the phospholipid; and the fluorescent sterol are in the form of mHDL, the fluorescent sterol is DHE, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of identifying an LCAT activating agent, the fluorescent sterol is DHE, the LCAT activity enhancer is an LCAT-activating peptide and the phospholipid is phosphatidylcholine. In another embodiment of a method of identifying an LCAT activating agent, the fluorescent sterol is DHE, the LCAT activity enhancer is a peptide selected from Table 1, and the phospholipid is phosphatidylcholine.

In another embodiment of a method of identifying an LCAT activating agent, the fluorescent sterol is DHE, the LCAT activity enhancer is an LCAT-activating peptide and the phospholipid is phosphatidylcholine. In another embodiment of a method of identifying an LCAT activating agent, the fluorescent sterol is DHE, the LCAT activity enhancer is a peptide selected from Table 1, and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of identifying an LCAT activating agent, the LCAT activity-enhancer, the phospholipid; and the fluorescent sterol are in the form of mHDL, the fluorescent sterol is cholestatrienol, the LCAT activity enhancer is an LCAT-activating peptide and the phospholipid is phosphatidylcholine; sphingomyelin phosphatidylethanolamine; dimethylphosphatidylethanolamine; phosphatidylserine; phosphatidylinositol; phosphatidylglycerol; cardiolipin, or a mixture thereof.

In another embodiment of a method of identifying an LCAT activating agent, the LCAT activity-enhancer, the phospholipid; and the fluorescent sterol are in the form of mHDL, the fluorescent sterol is cholestatrienol, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of identifying an LCAT activating agent, the fluorescent sterol is cholestatrienol, the LCAT activity enhancer is a peptide having a sequence selected from Table 1, and the phospholipid is phosphatidylcholine; sphingomyelin phosphatidylethanolamine; dimethylphosphatidylethanolamine; phosphatidylserine; phosphatidylinositol; phosphatidylglycerol; cardiolipin, or a mixture thereof.

In another embodiment of a method of identifying an LCAT activating agent, the fluorescent sterol is cholestatrienol, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9, and the phospholipid is phosphatidylcholine; sphingomyelin phosphatidylethanolamine; dimethylphosphatidylethanolamine; phosphatidylserine; phosphatidylinositol; phosphatidylglycerol; cardiolipin, or a mixture thereof.

In another embodiment of a method of identifying an LCAT activating agent, the LCAT activity-enhancer, the phospholipid; and the fluorescent sterol are in the form of mHDL, the fluorescent sterol is cholestatrienol, the LCAT activity enhancer is an LCAT-activating peptide and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of a method of identifying an LCAT activating agent, the fluorescent sterol is cholestatrienol, the LCAT activity enhancer is an LCAT-activating peptide and the phospholipid is phosphatidylcholine. In another embodiment of a method of determining the level of LCAT activity the fluorescent sterol is DHE, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9, and the phospholipid is phosphatidylcholine.

In another embodiment of the method of identifying an LCAT activating agent, wherein the fluorescent sterol is cholestatrienol, the LCAT activity enhancer is an LCAT-activating peptide and the phospholipid is phosphatidylcholine. In another embodiment of the method of identifying an LCAT activating agent, the fluorescent sterol is DHE, the LCAT activity enhancer is a peptide having a sequence selected from Table 1, and the phospholipid is egg phosphatidylcholine; soybean phosphatidylcholine; dipalmitoylphosphatidylcholine; dimyristoylphosphatidylcholine; 1-myristoyl-2-palmitoylphosphatidylcholine; 1-palmitoyl-2-myristoylphosphatidylcholine; 1-palmitoyl-2-oleoylphosphatidylcholine; dioleoylphosphatidylcholine; dipalmitoylphosphatidylcholine; 1-myristoyl-2-palmitoleoylphosphatidylcholine; 1-palmitoleoyl-2-myristoylphosphatidylcholine, 1-palmitoleoyl-2-oleoylphosphatidylcholine, dipalmitoleoylphosphatidylcholine; phosphatidylcholine; or a phosphatidylcholine wherein an oleyl alcohol, palmityl alcohol, palmitoleyl alcohol, or myristyl alcohol is linked by an ether bond to the sn-1 position of the phosphatidylcholine, or a mixture thereof.

In another embodiment of the method of identifying an LCAT activating agent, step d) further comprises adding a detergent, wherein the LCAT activity-enhancer, the phospholipid; and the fluorescent sterol are in the form of mHDL, the fluorescent sterol is DHE or cholestatrienol, and the LCAT activity enhancer is an LCAT-activating peptide.

In another embodiment of the method of identifying an LCAT activating agent, wherein the substrate further comprises a lipophilic antioxidant and step e) further comprises adding a detergent, wherein the LCAT activity-enhancer, the phospholipid; and the fluorescent sterol are in the form of mHDL, the fluorescent sterol is DHE or cholestatrienol, and the LCAT activity enhancer is an LCAT-activating peptide.

In yet another embodiment of the method of identifying an LCAT activating agent, wherein the substrate further comprises a lipophilic antioxidant and step e) further comprises adding a detergent, and a catalase, wherein the LCAT activity-enhancer, the phospholipid; and the fluorescent sterol are in the form of mHDL, the fluorescent sterol is DHE or cholestatrienol, the LCAT activity enhancer is an LCAT-activating peptide.

In yet another embodiment of the method of identifying an LCAT activating agent, wherein the substrate further comprises a lipophilic antioxidant and step e) further comprises adding a detergent, and a catalase, wherein the LCAT activity-enhancer, the phospholipid; and the fluorescent sterol are in the form of mHDL, the fluorescent sterol is DHE or cholestatrienol, the LCAT activity enhancer is an LCAT-activating peptide selected from Table 1.

In still another embodiment of the method of identifying an LCAT activating agent, wherein the substrate further comprises a lipophilic antioxidant and step e) further comprises adding a detergent, and a catalase and wherein the LCAT activity-enhancer, the phospholipid; and the fluorescent sterol are in the form of mHDL, the fluorescent sterol is DHE or cholestatrienol, the LCAT activity enhancer is a peptide having the sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 9. In another embodiment the peptide has the sequence of SEQ ID NO: 1. In another embodiment the peptide has the sequence of SEQ ID NO: 2. In another embodiment the peptide has the sequence of SEQ ID NO: 3. In another embodiment the peptide has the sequence of SEQ ID NO: 4. In another embodiment the peptide has the sequence of SEQ ID NO: 5. In another embodiment the peptide has the sequence of SEQ ID NO: 6. In another embodiment the peptide has the sequence of SEQ ID NO: 7. In another embodiment the peptide has the sequence of SEQ ID NO: 9.

EXAMPLES

Example 1

Elimination of DHE Fluorescence as a Result of Oxidation by Cholesterol Oxidase

Figure 3:
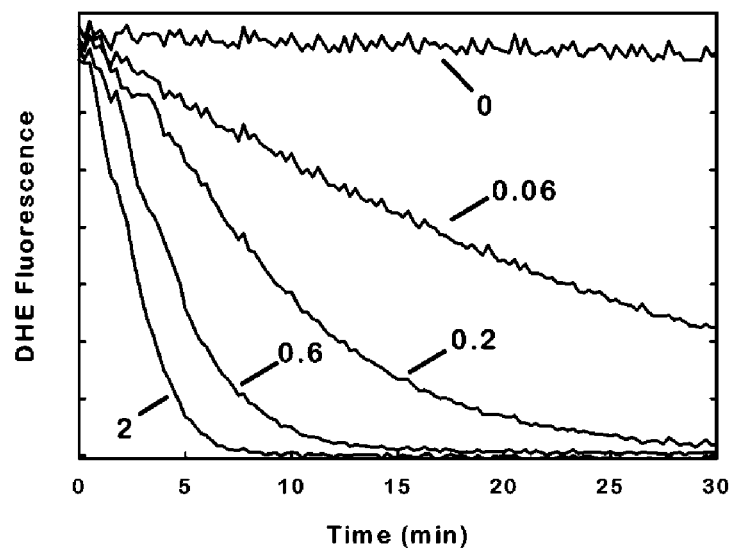
FIG. 3 is a graph showing the elimination of DHE fluorescence as a result of oxidation by cholesterol oxidase at various COx concentrations (U/ml).

To demonstrate the effect of DHE oxidation by COx on fluorescence, mHDL was prepared by combining 1 mole equivalent DHE (Sigma-Aldrich), 9 mole equivalents 1-palmitoyl-2-oleoyl-phosphatidylcholine (POPC) (Avanti Polar Lipids) and 2 mole equivalents LAP (SEQ ID NO: 1) in phosphate buffer (150 mM NaCl, 20 mM sodium phosphate, 1 mM ethylenediaminetetraacetic acid, pH 7.4). LAP, which was produced by solid-phase synthesis, was weighed into a glass vial and dissolved in 0.1 ml of methanol. Aliquots of stock solutions of DHE in chloroform and POPC in chloroform were mixed with the LAP. Solvents were removed by evaporation under a stream of nitrogen followed by 2 hours high vacuum. The vial contents were re-dissolved in a volume of buffer to yield 250 µM DHE. Cholesterol oxidase (*Streptomyces* sp.) (Sigma-Aldrich, St. Louis, Mo.) was dissolved in buffer containing 2% Triton X-100 to a final concentration of 50 U/ml. To a 96-well assay plate equilibrated to 37° C. in a Gemini SpectroMax fluorescence plate reader (Molecular Dynamics, Sunnyvale, Calif.) were added volumes of buffer, mHDL and COx to obtain 25 µM DHE, 0.5% Triton X-100, and the indicated amount of oxidase (U/ml). The fluorescence of sample wells was measured at timed intervals at 325 nm excitation and 425 nm emission wavelengths and including a 420 nm cutoff filter. (FIG. 3)

Example 2

Detection of Dehydroergosteryl Ester Formation Due to LCAT

Figure 4:
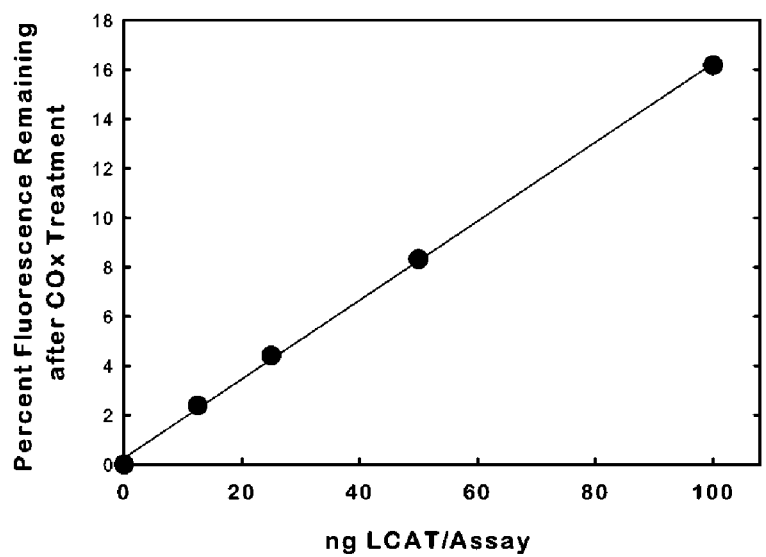
FIG. 4 is a graph showing the dependence of dehydroergosteryl ester formation on rhLCAT concentration detected by measurement of fluorescence remaining after unesterified DHE has been oxidized and rendered non-fluorescent by incubation with cholesterol oxidase.

Recombinant human LCAT (rhLCAT), isolated from cells expressing human LCAT (Example 5), was diluted into phosphate buffer containing 5 mM β-mercaptoethanol and 60 µM bovine serum albumin to obtain rhLCAT concentrations that would deliver the indicated mass of rhLCAT to assay samples in a 5 µL volume. Substrate, prepared as in Example 1, was diluted to 62.5 µM DHE with phosphate buffer containing 5 mM β-mercaptoethanol and 60 µM bovine serum albumin. One hundred microliter volumes of the diluted substrate were added to individual wells of a black, polystyrene 96-well plate (Whatman 7701-2350) which had previously been loaded with 5 µL of rhLCAT. Blank and control wells were not loaded with rhLCAT. The plate was covered and incubated at 37° C. for one hour. The reaction was quenched by the addition of 25 µL phosphate buffer containing 2% Triton X-100 and 5 units/ml COx (*Streptomyces* sp.) to all wells except control wells, which received 2% Triton X-100 without COx. The plate was returned to the incubator for one hour, then equilibrated to 37° C. in the plate reader and scanned for DHE fluorescence. Percent fluorescence was calculated from the ratio of the average fluorescence of duplicate wells treated with COx to the average fluorescence of the control wells. The amount of fluorescence remaining after oxidation is directly proportional to the amount of DHE esterified by LCAT. The line represents the fit of the data by linear regression. (FIG. 4).

Example 3

Figure 5:
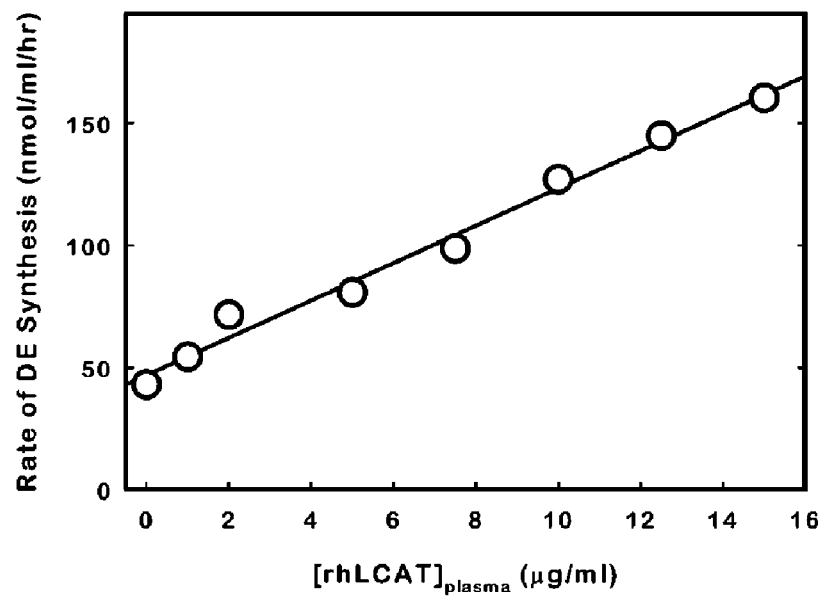
FIG. 5 is a graph of dehydroergosteryl ester (DE) formation detected in mouse plasma supplemented with increasing amounts of recombinant human LCAT added to the plasma.

Dehydroergosteryl Ester (DE) Formation Detected in Mouse Plasma Supplemented with Increasing Amounts of rhLCAT To demonstrate the ability of this invention to detect LCAT activity in plasma, mouse plasmas from transgenic mice expressing human apoA-I (Jackson Laboratories) were supplemented with 0 (control), 1, 2, 5, 7.5, 10, 12.5, or 15 µg/ml rhLCAT. Two microliter aliquots of plasma were added to separate assay wells followed by 100 microliters of substrate (Example 2). The assay plate was incubated for 2 hours at 37° C. followed by quenching with COx (Example 2). The nmoles DHE ester formed in each sample was calculated by subtracting the average fluorescence of the blank wells from the fluorescence of each sample well to obtain net fluorescence. The average net fluorescence of sample wells at each rhLCAT level was then divided by the average net fluorescence of control wells and multiplied by the DHE per well, which was 6.25 nmoles, to yield the nmoles of DHE ester formed. The line represents the fit of the data by linear regression. The activity detected at 0 µg/ml rhLCAT (Y-intercept) is the activity of endogenous mouse LCAT in the plasma (FIG. 5).

Example 4

Figure 6:
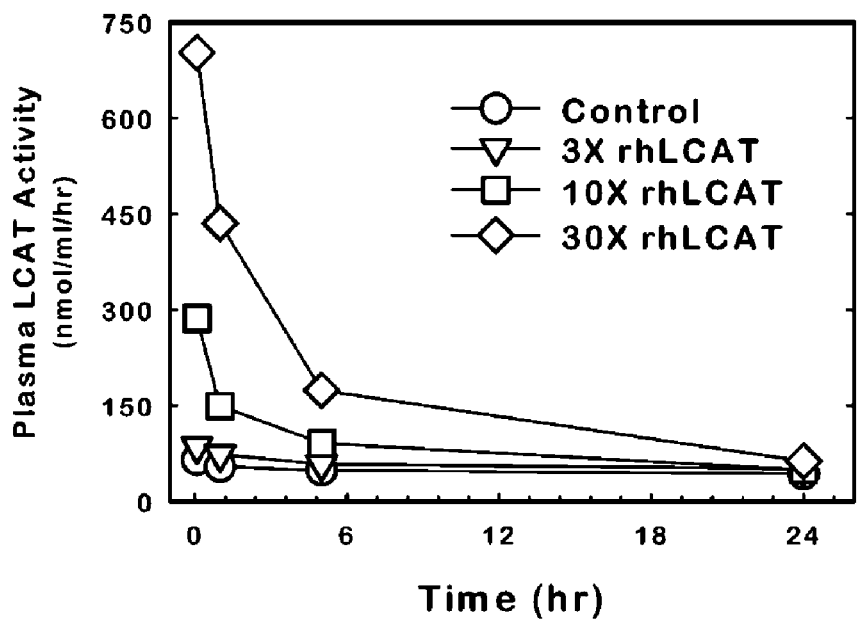
FIG. 6 shows a time course of LCAT activity in plasma from mice injected intravenously with various amounts of recombinant human LCAT at T=0 hours.

Time Course of LCAT Activity in Plasma from Mice Injected Intravenously with rhLCAT The utility of the current invention to measure LCAT activity changes in vivo as a result of rhLCAT injection is shown in FIG. 6. Transgenic mice expressing human apoA-I (Jackson Laboratories) and maintained on chow diet were injected (intravenous) with rhLCAT in normal saline at doses of 1 mg/kg (3×), 3 mg/kg (10×) or 10 mg/kg (30×). Control animals were injected with saline alone. Plasma was prepared from blood samples collected at 0.1, 1, 5 and 24 hours following LCAT injection. Two microliter plasma aliquots were assayed for LCAT activity as indicated for Example 3, but without the addition of further rhLCAT to plasma samples. The results demonstrate an 11-fold increase in LCAT activity in plasma collected at 1 hour post-dose from mice injected with the largest dose (30×). The rise in plasma LCAT activity at 1 hour was correspondingly lower in plasma from mice dosed with less rhLCAT. The plasma LCAT activity declined with time, thereby providing evidence of rhLCAT clearance kinetics (FIG. 6).

Example 5

Preparation of Recombinant LCAT

The plasmid pCMV6-XL4/LCAT encoding human LCAT protein was purchased from Origene Technologies and ligated into pcDNA3.1/Hygro (Invitrogen, Carlsbad, Calif.). The pcDNA3.1 vector was transfected into HEK293f cells. Stably-transfected cells were selected with 200 µg/ml hygromycin B and grown in Freestyle 293 serum-free medium (Invitrogen) in 10 L shake flasks for 4 days. The rhLCAT was isolated from the culture medium by precipitation with zinc chloride followed by batch capture with phenylsepharose and gradient elution from 150 mM NaCl in 25 mM phosphate (pH 7.2) to pure water.

Example 6

Preparation and Testing of Peptide Substrate (mHDL)

LCAT-activating peptides, which are produced by solid-phase synthesis (GenScript USA, Inc), are dissolved in methanol at 5 mM concentration. Three hundred and ninety seven microliters of 5 mM LAP and 357 microliters of a chloroform solution containing 25 mM POPC and 2.8 mM DHE are added to a glass vial. The solvents are evaporated by directing a gentle stream of inert gas (e.g. nitrogen) into the vial. Residual solvent is removed by high vacuum for 2 hours. The dried mixture is dispersed in 2 milliliters of phosphate buffer (150 mM NaCl, 50 mM sodium phosphate, 1 mM EDTA, pH 7.4) to obtain a final DHE concentration of 0.5 mM. The vial is flushed with inert gas and capped after buffer addition. The dispersion is obtained by vortexing and brief (10 to 30 seconds) sonication in a water bath sonicator. The substrate is protected from light and stored with inert gas in the capped vial at 2-8° C.

This substrate preparation procedure is suitable for any LAP that can form a stable micelle complex with phospholipid and sterol. mHDL can also be prepared with fluorescent sterols other than DHE according to Example 6.

The LCAT activating potential of LAP is determined with the protocol described in Example 2 at a DHE concentration of 50 µM and with the rhLCAT concentrations indicated. A linear regression fit of nmoles DHE ester formed, calculated as in Example 3, versus rhLCAT in the sample yields the specific activity (nmol DHE ester/µg LCAT/hour) of rhLCAT with substrate. This protocol was used to compare and characterize the LCAT activating potential of amphipathic peptides with mean hydrophobicities and mean hydrophobic moments that were sufficient to enable the peptides to form stable micelle complexes with phosphatidylcholine and DHE (Table 3).

TABLE 3

| EFFECT OF PEPTIDE SEQUENCE ON LCAT ACTIVITY | | | | |
|---|---|---|---|---|
| SEQ ID NO: | AMINO ACID SEQUENCE | $<H>$ [1] | $<\mu_H>$ [2] | RELATIVE ACTIVITY [3] |
| 1 [4] | P V L D L F R E L L N E L L E A L K Q K L K | -1.08 | 0.91 | 100 |
| 2 | P T L D L F R E L L N E L L E A L K Q K L K | -1.12 | 0.88 | 94 |
| 3 | P S L D L F R E L L N E L L E A L K Q K L K | -1.13 | 0.87 | 87 |
| 4 | P V L D L F R E L L N E L L Q K L K K | -1.13 | 0.99 | 86 |
| 5 | P T L D L F R E L L N E L L Q K L K K | -1.17 | 0.96 | 65 |
| 6 | P V L D L F R E L L E E L L Q K L K K | -1.16 | 1.02 | 65 |
| 7 | Ac-P V L D L F K E L L E E L F Q K L K K-NH$_2$ [5] | -1.06 | 1.01 | 56 |
| 8 | Ac-P V L D K F L E L L E E L F Q K L K K-NH$_2$ | -1.06 | 1.09 | 15 |
| 9 | Ac-E W L K A F L E K V L E K L K E L F-NH$_2$ | -0.87 | 0.82 | 55 |
| 10 [6] | Ac-E W L K A F Y E K V L E K L K E L F-NH$_2$ | -0.94 | 0.77 | 43 |
| 11 [7] | Ac-D W L K A F Y D K V F E K F K E F F-NH$_2$ | -1.07 | 0.83 | 28 |
| 12 | E V L K N L L E K L L E K L K E L F | -1.05 | 0.94 | 21 |
| 13 | D L W Q R L L E L F N E L L E K L K Q A L K | -1.11 | 1.03 | 0 |
| 14 | D V F Q A L K E L F A Q L L E K W K Q V | -1.04 | 0.85 | 0 |

[1] Mean hydrophobicity. Sum of amino acid hydrophobicities according to hessa et al. (2005, Nature 433: 377-381.) divided by number of residues.
[2] Mean hydrophobic moment (Pownall et al., 1983, FEBS 159(1, 2): 17-23.).
[3] Percent activity relative to SEQ ID: 1.
[4] Peptide 4 (Dasseux et al., US7273848).
[5] Peptide terminal modifications are indicated by Ac- for acetylated N-terminus and by —NH$_2$ for amidated C-terminus.
[6] [Glu$^{1,8}$, Leu$^{11,17}$] 18A peptide (Expand et al., 1987, J. Biol. Chem. 262(19): 9389-9396).
[7] 5F peptide (Datta et al., 2001, J. Lipid Res. 42(7): 1096-1104).

Example 7

Preparation of Reconstituted HDL (rHDL) Substrate Containing DHE

A suitable method for preparing rHDL is as follows. Three hundred and fifty seven microliters of a chloroform solution containing 25 mM POPC and 2.8 mM DHE is added to a glass vial. The solvent is removed by evaporation under a gentle stream of inert gas (e.g. $N_2$) followed by at least 2 hours of high vacuum. The dried mixture is dispersed in 1 milliliter of 10 mM sodium cholate in phosphate buffer, sealed under inert gas and left standing at 4° C. for 1-2 hours until clear. A 0.25 milliliter volume of 10 mg/ml apoA-I in phosphate buffer is added to the lipid/cholate solution which is incubated under inert gas at 4° C. for an additional 12-16 hours. Apolipoprotein A-I is prepared from normal plasma or purchased from commercial sources (e.g. Biomedical Technologies, Inc.). The solution is transferred to a dialysis bag (10,000 MW cutoff) and dialyzed against 1 liter of phosphate buffer for 16-20 hours. The dialysis is repeated 2 times. The amount of DHE in the resultant preparation is determined by its fluorescence relative to a standard and diluted to a final DHE concentration of 0.5 mM with phosphate buffer. Types of apoA-I suitable for rHDL preparation include apoA-I isolated from mammalian plasma and natural and man-made apoA-I variants, and naturally occurring genetic variants such as apoA-I (Milano), apoA-I (Paris), and apoA-I (Oslo).

Example 8

Assay of LCAT in Aqueous Solution

This embodiment of the assay is suitable for determining LCAT activity in lipoprotein-free samples or samples with a low lipoprotein content that does not interfere with DHE esterification. The samples may, for example, be preparations of LCAT purified from plasmas or cell culture media containing LCAT or samples from chromatographic separations. The reaction solution for the assay is prepared by combining 1 volume of mHDL or rHDL containing 0.5 mM DHE with 9 volumes of reaction buffer (5 mM β-mercaptoethanol, 60 mM bovine serum albumin in phosphate buffer). Sample aliquots of 1 to 10 microliters containing 5 to 200 nanograms of LCAT are added to individual wells of black polystyrene multi-well assay plates (e.g. Whatman 7701-2350). A separate group of wells are designated the blank and control wells and do not receive LCAT. The assay is begun by adding 100 microliters reaction solution to all assay wells followed by brief agitation and subsequent placement of the covered plate in a 37° C. incubator. The reaction time can vary but 60 minutes works well for the LCAT quantities indicated. At the end of the reaction time, 25 microliters of stop solution is added to all but the control wells. The stop solution is composed of 5 units/ml COx (*Streptomyces* sp.) in phosphate buffer containing 2% Triton X-100. The control wells receive 25 microliters of 2% Triton X-100 in phosphate buffer without COx. The plate is re-incubated at 37° C. for a period sufficient to oxidize all unesterified DHE (e.g. 30-60 min) and then scanned for fluorescence in a fluorescence plate reader set at suitable wavelengths for DHE excitation (e.g. 325 nm) and emission (e.g. 395 nm). The wavelengths for optimal signal to noise ratio are dependent on the model of plate reader used. Plate readers that exhibit a low signal to noise ratio at the excitation and emission maxima of DHE at approximately 325 nm and 395 nm, respectively, are the most well suited. The amount of DHE ester product formed in a test well is calculated from the net fluorescence of test wells (test fluorescence−blank fluorescence) divided by the net fluorescence of the control wells (control fluorescence−blank fluorescence) times the DHE content of the control wells. The fluorescence from the control wells provides the instrument response per unit of DHE.

Example 9

Assay of LCAT in Plasma or Serum

A 2 microliter volume of each serum or plasma sample is combined with 100 microliters of reaction solution (comprising either mHDL or rHDL), as described above. The samples are incubated for 3 hours at 37° C. The remainder of the procedure as the same as that described above for aqueous LCAT samples.

Example 10

Detection of LCAT Activity in Human Plasma Following Phosphotungstic Acid/Magnesium Chloride Precipitation of Non-HDL Lipoproteins To demonstrate the improved assay performance in HDL-enriched plasma, LCAT activity was determined in normal human plasma before and after precipitation of non-HDL lipoproteins. For precipitation, a 10 μl aliquot of 4% phosphotungstic acid (pH 6.15) was added to 100 μl of human plasma at room temperature. This was followed by the addition of 2.5 μl of 2M $Mg_2Cl_2$ and mixing. After letting the amended plasma stand for 10 min, the plasma was centrifuged at 6000×g for 10 minutes. Five microliter aliquots of the untreated and precipitated plasma were tested with the fluorescent LCAT assay, in triplicate. The assay was performed essentially as described in Example 2 with the exceptions that DHE concentration was 100 μM and the LCAT incubation time was 2 hours. The results are presented in FIG. 7.

What is claimed is:

1. A method of determining the level of LCAT activity in an assay sample comprising:
   a) providing a synthetic substrate comprising
      1) a phospholipid;
      2) a fluorescent sterol; and
      3) an LCAT activity-enhancer;
   b) contacting the synthetic substrate with the assay sample to yield an assay mixture;
   c) incubating the assay mixture for a period of time;
   d) adding a COx enzyme to the assay mixture;
   e) measuring the fluorescence level of the assay mixture; and
   f) determining the LCAT activity in the sample.

2. The method of claim 1, wherein step d) further comprises adding a detergent.

3. The method of claim 1, wherein step d) further comprises adding a catalase.

4. The method of claim 1, wherein the sample is plasma.

5. The method of claim 1, wherein the sample is serum.

6. The method of claim 1, wherein apolipoprotein B-containing lipoproteins are removed from the sample before incubating the mixture of the sample and the LCAT substrate.

7. The method of claim 6, wherein the apolipoprotein B-containing lipoproteins are removed by precipitation.

* * * * *